United States Patent [19]
Rhee et al.

[11] Patent Number: 6,090,964
[45] Date of Patent: Jul. 18, 2000

[54] ORGANOCUPROUS PRECURSORS FOR CHEMICAL VAPOR DEPOSITION OF A COPPER FILM

[75] Inventors: Shi-Woo Rhee, Pohang; Doo-Hwan Cho, Chilgok-gun; Jai-Wook Park, Pohang; Sang-Woo Kang, Seoul, all of Rep. of Korea

[73] Assignee: Postech Foundation, Rep. of Korea

[21] Appl. No.: 09/233,573

[22] Filed: Jan. 19, 1999

[30] Foreign Application Priority Data

Jan. 19, 1998 [KR] Rep. of Korea .................. 98-1388

[51] Int. Cl.$^7$ ............................. C07F 1/08; C23C 16/18
[52] U.S. Cl. ........................ 556/117; 556/112; 427/252
[58] Field of Search ..................... 556/112, 117; 427/252

[56] References Cited

U.S. PATENT DOCUMENTS

| | | | |
|---|---|---|---|
| 5,144,049 | 9/1992 | Norman et al. | 556/12 |
| 5,449,799 | 9/1995 | Terfloth et al. | 556/112 |
| 5,663,391 | 9/1997 | Machida et al. | 556/12 |
| 5,767,301 | 6/1998 | Senzaki et al. | 556/9 |

*Primary Examiner*—Porfirio Nazario Gonzalez
*Attorney, Agent, or Firm*—Anderson Kill & Olick

[57] ABSTRACT

A liquid organocuprous compound of formula (I) of the present invention can be conveniently used in a low-temperature CVD process for the production of a contaminant-free copper film having good step-coverage and hole-filling properties:

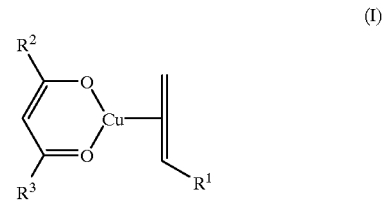

wherein:
$R^1$ represents a $C_{3-8}$ cycloalkyl group, and
$R^2$ and $R^3$ are each independently a perfluorinated $C_{1-4}$ alkyl group.

4 Claims, 8 Drawing Sheets

(a)

(b)

(c)

ORGANOCUPROUS PRECURSORS FOR CHEMICAL VAPOR DEPOSITION OF A COPPER FILM

FIELD OF THE INVENTION

The present invention relates to novel, highly volatile organocuprous precursors which are useful in the chemical vapor deposition of a copper film having good step-coverage and hole-filling properties; and to a process for the preparation of a copper film using same.

BACKGROUND OF THE INVENTION

Hitherto, many metals such as tungsten and aluminum have been widely used as interconnecting materials in many electronic devices such as semiconductors. However, an aluminum interconnect (specific resistance: about 2.7 $\mu\Omega$.cm) tends to be hampered by the problem of electromigration, while tungsten has the problem of high resistivity (specific resistance: about 5.4 $\mu\Omega$.cm). Therefore, attempts have recently been made to use copper which is highly conductive (specific resistance: about 1.67 $\mu\Omega$.cm) and electromigration resistant, as an interconnecting material in advanced devices such as ultra-large semiconductor integrated circuits.

A metallic interconnect is typically formed by a chemical vapor deposition (CVD) method using a metallorganic precursor compound, and Cu films have previously been prepared using various organic copper precursors such as $Cu(II)(hfac)_2$, wherein hfac stands for hexafluoroacetylacetonate. However, a CVD process using such Cu(II) precursors requires a high deposition temperature and the resulting Cu film is often contaminated by various impurities.

Organic copper(I) precursor compounds usable in a low temperature, selective CVD process have been recently developed. For example, the use of organocuprous precursors such as (hfac)Cu(I) (vinyltrimethylsilane) and (hfac)Cu(I) (allyltrimethylsilane) in a low temperature CVD process to selectively deposit a Cu film on a conductive substrate surface has been disclosed by Norman et al. in U.S. Pat. No. 5,085,731. However, the CVD using the above Cu(I)-vinylsilane precursors provides copper films having poor step-coverage and hole-filling characteristics.

U.S. Pat. No. 5,098,516 teaches the use of Cu(I)-olefin precursors such as (hfac)Cu(I).COD (COD: cyclooctadiene) and (hfac)Cu(I).NBD (NBD: norbonadiene) in a low temperature CVD process. The above Cu(I)-olefin precursors are solids, and for their vaporization, they are sublimed at a temperature below their thermal decomposition temperatures, e.g., about 105° C. for (hfac)Cu(I).COD. Thus, the CVD process; disclosed in U.S. Pat. No. 5,098,516 is hampered by the difficult problem of handling solid precursors in a mass production system. Moreover, the CVD of a copper film using, e.g., (hfac)Cu(I).COD requires a relatively high substrate temperature of above 150° C. and the resulting copper film is often of poor quality.

SUMMARY OF THE INVENTION

Accordingly, it is a primary object of the present invention to provide a liquid organic copper(I) precursor which can be conveniently used in a low-temperature CVD process for the production of a contaminant-free copper film having good step-coverage and hole-filling properties.

In accordance with one aspect of the present invention, there is provided an organocuprous compound of formula (I)

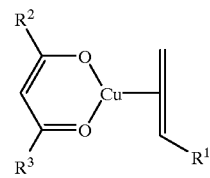

wherein:
$R^1$ represents a $C_{3-8}$ cycloalkyl group, and
$R^2$ and $R^3$ are each independently a perfluorinated $C_{1-4}$ alkyl group.

In accordance with another aspect of the present invention, there is provide d a process for depositing a copper film on a substrate, which comprises vaporizing the compound of formula (I) at a temperature ranging from 15 to 60° C. and bringing the resulting vapor into contact with the substrate heated to a temperature ranging from 70 to 250° C.

BRIEF DESCRIPTION OF THE DRAWINGS

The above and other objects and features of the present invention will become apparent from the following description of the invention taken in conjunction with the accompanying drawings, in which.

DETAILED DESCRIPTION OF THE INVENTION

Figure 1:
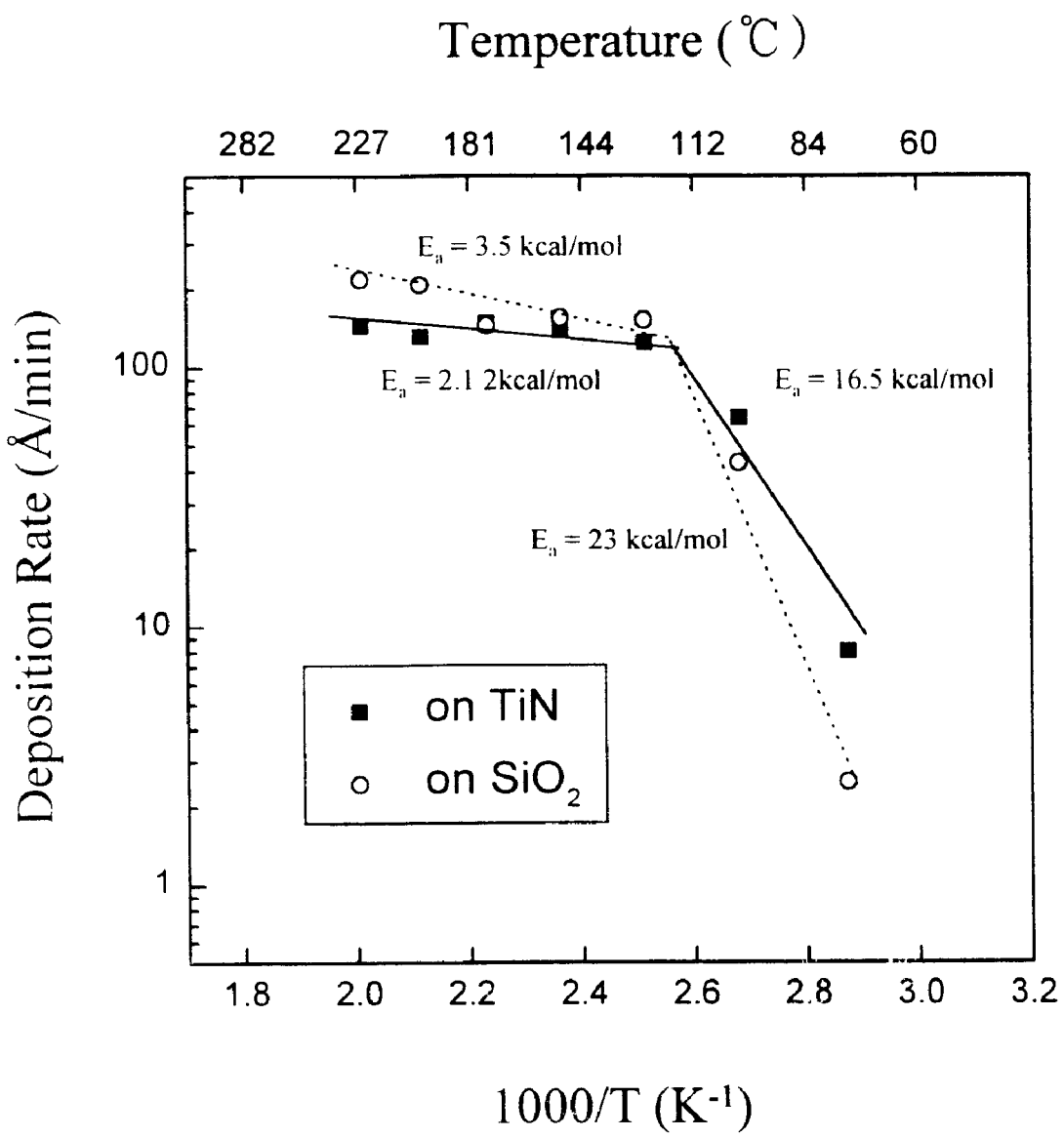
FIG. 1 shows the dependence of the Cu deposition rate on the substrate temperature in a CVD process using the inventive organocuprous precursor.

Among the compounds of formula (I) according to the present invention, preferred are those represented by formula (I-a)

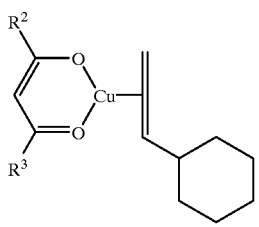

(I-a)

wherein

R² and R³ are the same as defined above, preferably trifluoromethyl group.

When R² and R³ are each a trifluoromethyl group, the compound of formula (I) may be prepared by reacting 1,1,1,5,5,5-hexafluoro-2,4-pentanedione (Hhfac), a vinylcycloalkane and cuprous oxide ($Cu_2O$) in the presence of an organic solvent, e.g., an ether or dichloromethane. This reaction may be conducted at a temperature ranging from 0 to 20° C. under an ambient pressure for 30 to 60 minutes. The reactants may be preferably employed in a Hhfac: vinylcycloalkane: $Cu_2O$ molar ratio of about 2:2:1.

The compound of formula (I) according to the present invention has good thermostability and high volatility, and in a CVD process for the formation of a copper film on a specified surface of a substrate, it may be conveniently volatilized in a bubbler at a temperature ranging from about 15 to 60° C. Alternatively, the liquid compound of formula (I) may be employed in a direct liquid injection (DLI) system.

The CVD process for the formation of a copper thin film using the inventive organocuprous precursor may be carried out in a conventional manner, e.g., by vaporizing the inventive precursor and conveying the resulting vapor with a carrier gas such as argon to a substrate, e.g., platinum, silica or TiN, heated to a temperature ranging from 70 to 250° C., preferably 70 to 110° C. under a reduced pressure, e.g., 0.1 to 10 torr. The thickness of the copper film may be conveniently controlled by adjusting the deposition time.

The following Examples are intended to further illustrate the present invention without limiting its scope.

EXAMPLE 1

Synthesis of Cu(hexafluoroacetylacetonate) vinylcyclohexane: (hfac)Cu(I)(VCH)

0.5 g (3.5 mmol) of $Cu_2O$ and 0.84 g (3.5 mmol) of $MgSO_4$ were charged to a Schlenk flask and thereto was added 30 ml of diethyl ether which had been previously distilled from sodium benzophenone under an argon atmosphere. The resulting mixture was cooled to 0° C. and added thereto was 0.78 g (7.0 mmol) of vinylcyclohexane. The resulting reddish suspension was stirred for 30 minutes, and slowly added thereto was a solution of 1.46 g (7.0 mmol) of 1,1,1,5,5,5-hexafluoro-2,4-pentanedione(Hhfac) in diethyl ether with a canula. The resulting mixture was stirred until the color of the mixture changed from yellow to green. The resulting solution was filtered through a bed of CELLITE™ and the solvent was removed therefrom under a reduced pressure to obtain 1.13 g of the titled compound as a green liquid (yield 85%).

$^1$H-NMR ($CDCl_3$, ppm) δ 6.13(s, 1H, hfac proton), 5.29 (m, 1H, $CH_2$=CH—), 4.33(dd, 2H, $CH_2$=CH—), 1.66–1.97(m, 6H, cyclohexyl), 1.08–1.35(m, 5H, cyclohexyl).

$^{13}$C-NMR ($CDCl_3$, ppm) δ 178.33(q, 33.7 Hz, $CF_3COOH$), 117.92(q, 277.5 Hz, —$CF_3$), 114.79 ($CH_2$=CH—), 90.34(COCHCO), 79.09 ($CH_2$=CH—), [42.22, 33.65, 26.31, 26.17(cyclohexyl)].

The titled compound in its liquid form was found to be stable indefinitely at 60° C. This should be contrasted with the thermal instability of the liquid form of the prior art precursor, (hfac)Cu(I)(allyltrimethylsilane), at 60° C.

EXAMPLE 2

Synthesis of Cu(hexafluoroacetylacetonate) vinylcyclopentane: (hfac)Cu(I)(VCP)

The procedure of Example 1 was repeated using vinylcyclopentane in place of vinylcyclohexane to obtain the titled compound as a bluish green liquid in a yield of 75%.

$^1$H-NMR ($CDCl_3$, ppm) δ 6.10(s, 1H, hfac proton), 5.35 (m, 1H, $CH_2$=CH—), 4.38(m, 2H, $CH_2$=CH—), 2.39(m, 1H, cyclopentyl), 1.86(m, 2H, cyclopentyl), 1.68(m, 2H, cyclopentyl), 1.44(m, 4H, cyclopentyl).

$^{13}$C-NMR ($CDCl_3$, ppm) δ 178.52(q, $CH_3COCH$), 120.11 (q, —$CF_3$), 117.06($CH_2$=CH—), 90.12(COCHCO), 83.59 ($CH_2$=CH—) [45.16,34.01, 26.01(cyclopentyl)]

EXAMPLE 3

Deposition of a Copper Film on a Substrate

A copper film was formed on a TiN or $SiO_2$-coated substrate by a CVD process. Specifically, the compound synthesized in Example 1 was fed to a bubbler maintained at 45° C. The resulting vapor stream was conveyed together with an argon carrier gas at a flow rate of 50 sccm to the surface of the substrate positioned in a CVD chamber under a pressure of 0.3 mmHg.

Figure 2:
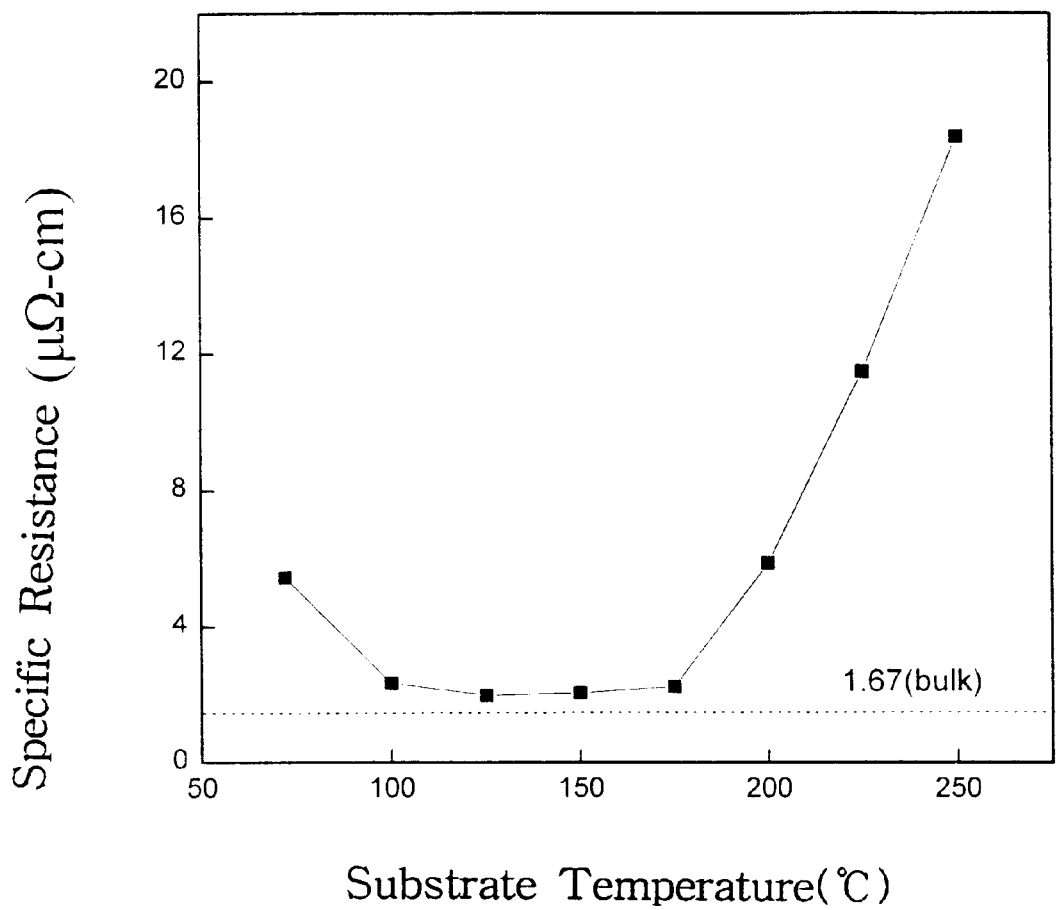
FIG. 2 presents the change in the specific resistance of copper films derived from the inventive precursor with the substrate temperature.

The deposition rate of the copper film and the specific resistance of the deposited film depending on the substrate temperature were measured, and the results are shown in FIGS. 1 and 2, respectively.

FIG. 1 shows that the copper film starts to form even at a low substrate temperature of 75° C. The deposition rate increases rapidly until the substrate temperature reaches 120° C., but it increases only very slowly at above 125° C. Further, it can be seen from FIG. 2 that the specific resistance of the film deposited at a substrate temperature of 100° C. to 175° C. approximately reaches that of bulk copper (about 1.67 μΩ.cm).

Figure 3:
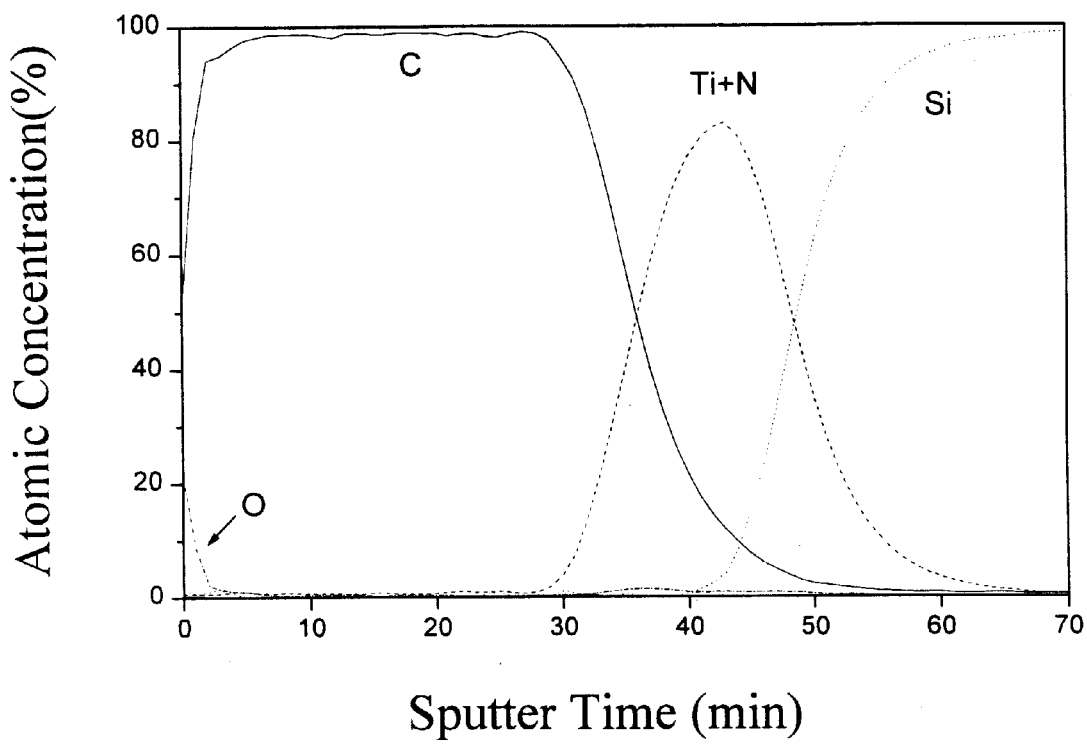
FIG. 3 depicts the elemental composition of a copper film derived from the inventive precursor, analyzed by Auger electron spectroscopy.

The copper film deposited at 125° C. was analyzed by Auger electron spectroscopy to determine its depth profile in terms of elemental composition, and the result in FIG. 3 demonstrates that the copper film deposited in accordance with the present invention is exceptionally pure, containing no significant amounts of impurities such as O, F and C.

Figure 4:
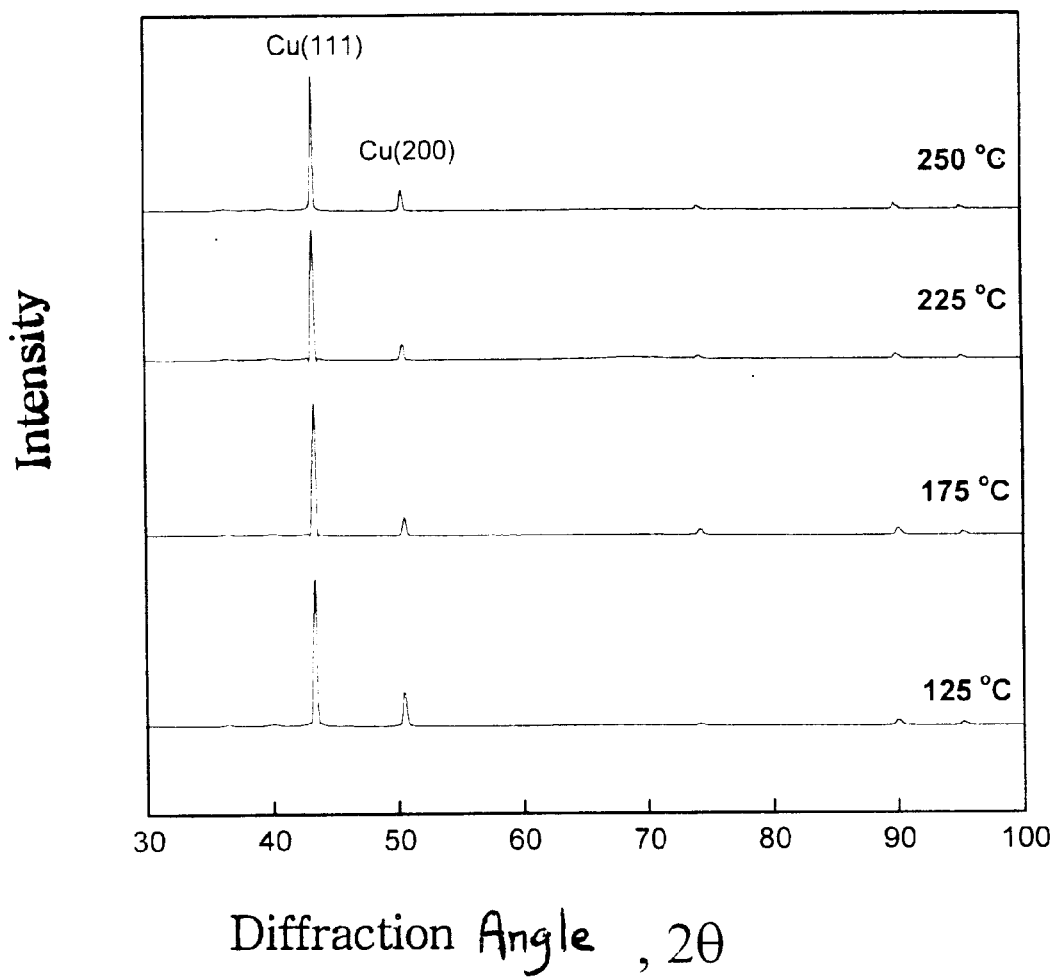
FIG. 4 reproduces XRD traces of copper films deposited at various temperatures using the inventive precursor.

Further, in order to determine the crystallinity of the copper film deposited in accordance with the present invention, each of the films deposited at 125, 175, 225 and 250° C. was analyzed with a X-ray diffractometer and the result in FIG. 4 shows that the copper film deposited onto the substrate in accordance with the present invention has preferential (111) orientation, with a minor degree of (200) orientation. The higher the (111) to (200) intensity ratio is, an interconnect made of the film becomes more resistant to the occurrence of short. Accordingly, it is clear that the copper film deposited in accordance with the present invention has excellent physical properties.

Figure 5:
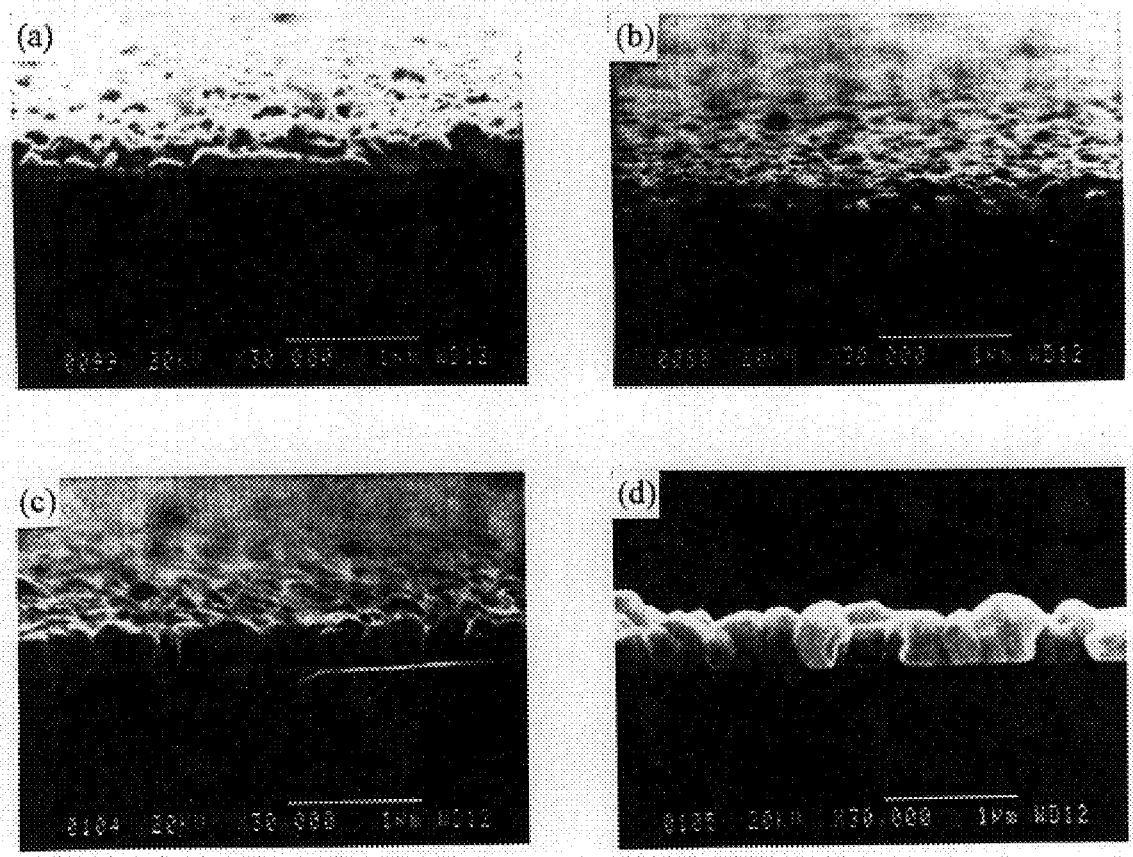
FIG. 5 illustrates XSEM photographs of copper films derived from the inventive precursor.

FIG. 5 illustrates XSEM (cross-sectional SEM) photographs of four copper films (3,000 Å thick) deposited at 100, 150, 225 and 250° C., respectively ((a): substrate temperature(Ts)=100° C., (b): Ts=150° C., (c): Ts=225° C., and (d): Ts=250° C.). From the shape and size of crystals, it can be seen that the deposited films exhibit good step coverage.

COMPARATIVE EXAMPLE 1

Figure 6:
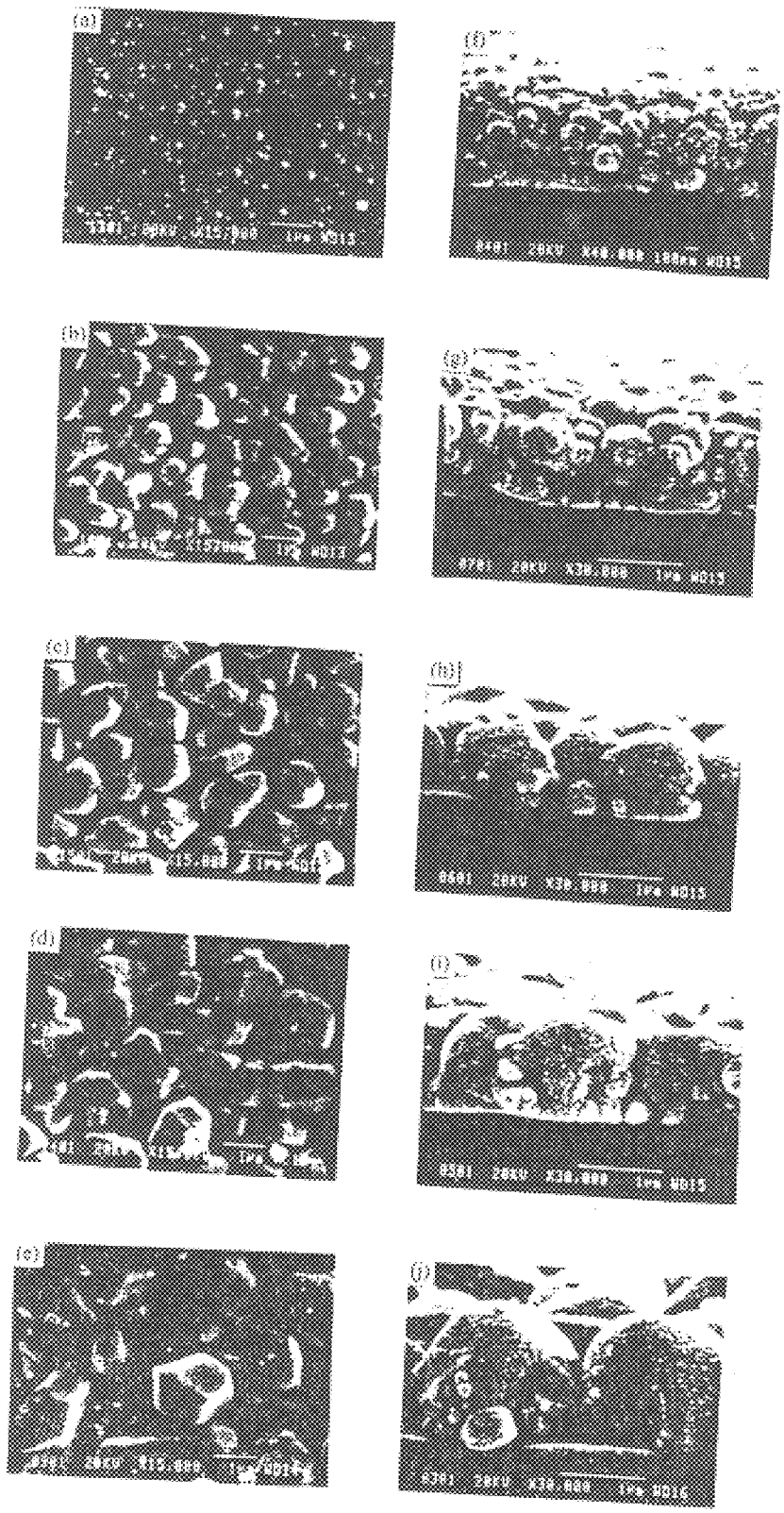
FIG. 6 shows SEM and XSEM photographs of copper films derived from (hfac)Cu(allyltrimethylsilane)

For a comparative purpose, the above-mentioned film deposition procedure was repeated employing Cu(hexafluoroacetylacetonate)allyltrimethylsilane in place of the inventive precursor at substrate temperatures of 75, 125, 175, 225 and 275° C. The SEM and XSEM photographs of the deposited films are shown in FIG. 6 ((a),(f): Ts=75° C., (b),(g): Ts=125° C., (c),(h): Ts=175° C., (d),(i): Ts=225° C., and (d),(j): Ts=275° C.). By comparing FIG. 5 with FIG. 6, it should become clear that the copper film derived from the inventive organocuprous compound gives a better step coverage than that derived from the prior art compound.

EXAMPLE 4

Deposition of Copper in Substrate Holes

Figure 7:
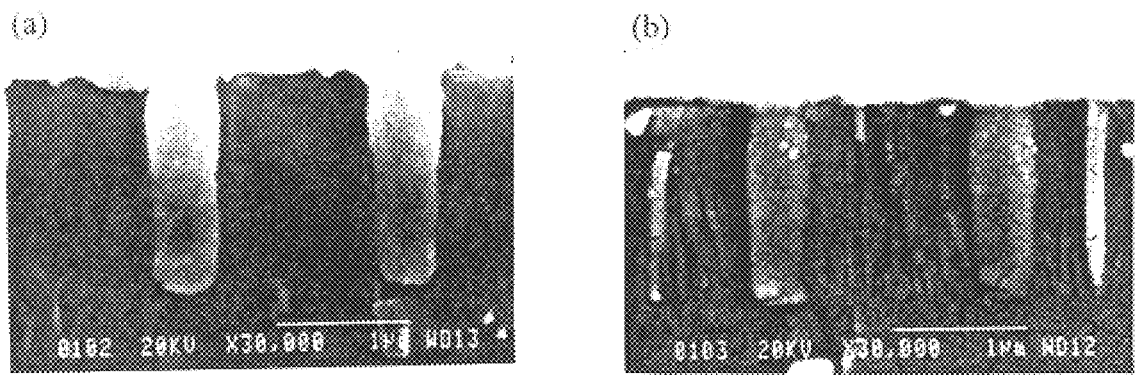
FIGS. 7 and 8 represent XSEM photographs of copper films deposited in a hole-containing substrate using the inventive precursor and (hfac)Cu(allyltrimethylsilane), respectively.

The CVD procedure of Example 3 was repeated except that a TiN-coated substrate having contact holes of a depth of 1.3 μm and a width of 0.3 μm was employed to fill the holes with metallic copper. FIG. 7 shows XSEM photographs of the hole-filled substrates produced by CVD at 100 and 125° C. ((a): Ts=100° C. and (b): Ts=125° C.), and it is clear that the inventive compound provides excellent hole-filling.

COMPARATIVE EXAMPLE 2

Figure 8:
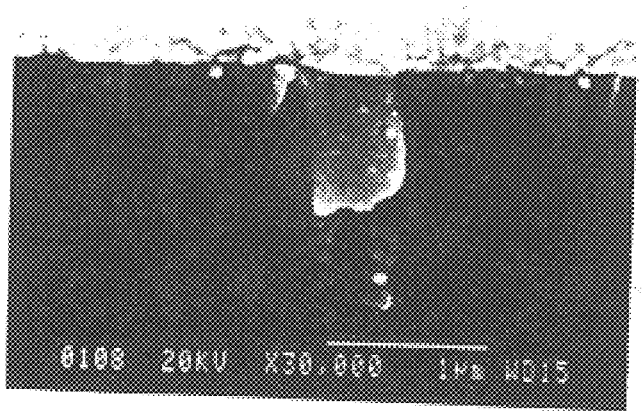
Figure 8:
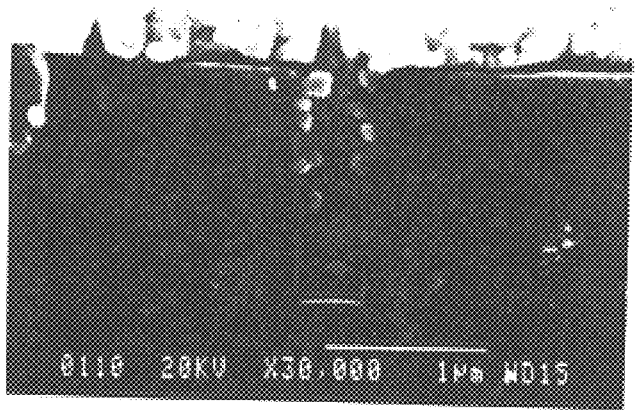
Figure 8:
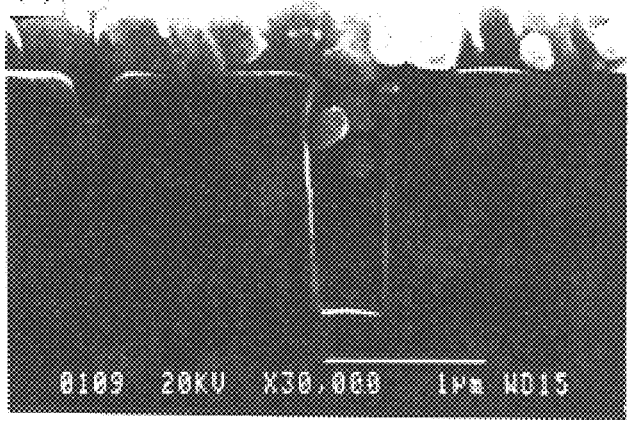

The procedure of Example 4 was repeated using Cu(hexafluoroacetylacetonate)allyltrimethylsilane in place of the inventive precursor compound at substrate temperatures of 75, 125 and 175° C., and XSEM photographs of the deposited substrates are shown in FIG. 8 ((a): Ts=75° C., (b): Ts=125° C. and (c): Ts=175° C.).

By comparing FIG. 7 with FIG. 8, it can be concluded that the inventive organocuprous precursor provides a better hole-filling capability than the prior art compound.

While the invention has been described with respect to the above specific embodiments, it should be recognized that various modifications and changes may be made to the invention by those skilled in the art which also fall within the scope of the invention as defined by the appended claims.

What is claimed is:

1. An organocuprous compound of formula (I)

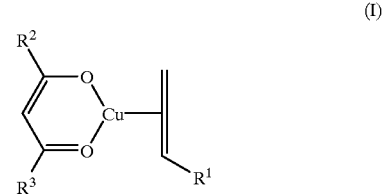

(I)

wherein:

$R^1$ represents a $C_{3-8}$ cycloalkyl group, and $R^2$ and $R^3$ are each independently a perfluorinated $C_{1-4}$ alkyl group.

2. The compound of claim 1 wherein $R^1$ is cyclohexyl.

3. A process for depositing a copper film on a substrate, which comprises vaporizing the compound recited in claim 1 at a temperature ranging from 15 to 60° C. and bringing the resulting vapor into contact with the substrate heated to a temperature ranging from 70 to 250° C.

4. The process of claim 3 wherein the substrate was heated to a temperature ranging from 70 to 110° C.

* * * * *